United States Patent
Eguchi et al.

(10) Patent No.: US 9,716,835 B2
(45) Date of Patent: Jul. 25, 2017

(54) BIOLOGICAL INFORMATION ACQUIRING DEVICE

(71) Applicant: SEIKO EPSON CORPORATION, Tokyo (JP)

(72) Inventors: Tsukasa Eguchi, Nagano (JP); Kimitake Mizobe, Pittsburgh, PA (US); Hirokazu Kasahara, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 13 days.

(21) Appl. No.: 14/870,648

(22) Filed: Sep. 30, 2015

(65) Prior Publication Data
US 2016/0098834 A1     Apr. 7, 2016

(30) Foreign Application Priority Data

Oct. 7, 2014   (JP) ................................ 2014-206461

(51) Int. Cl.
| | |
|---|---|
| *G06K 9/00* | (2006.01) |
| *A61B 5/00* | (2006.01) |
| *H04N 5/232* | (2006.01) |
| *A61B 5/145* | (2006.01) |
| *A61B 5/1455* | (2006.01) |

(Continued)

(52) U.S. Cl.
CPC ......... *H04N 5/23293* (2013.01); *A61B 5/004* (2013.01); *A61B 5/1455* (2013.01); *A61B 5/14532* (2013.01); *A61B 5/14552* (2013.01); *A61B 5/489* (2013.01); *H04N 5/232* (2013.01); *A61B 5/021* (2013.01); *A61B 5/681* (2013.01); *A61B 5/7425* (2013.01); *A61B 5/7475* (2013.01); *A61B 2560/0462* (2013.01);

(Continued)

(58) Field of Classification Search
CPC ............... G06K 9/00; G04N 5/00; A61B 5/00
USPC ....... 382/128, 129, 130, 131, 132, 133, 134; 600/309, 310, 322, 347, 368, 381, 465, 600/500
See application file for complete search history.

(56) References Cited

U.S. PATENT DOCUMENTS

| | | | |
|---|---|---|---|
| 6,349,227 B1 * | 2/2002 | Numada | A61B 5/061 600/309 |
| 6,672,739 B1 * | 1/2004 | Argyle | G02B 27/0994 362/259 |

(Continued)

FOREIGN PATENT DOCUMENTS

| | | |
|---|---|---|
| JP | 2000-189391 A | 7/2000 |
| JP | 2000-339445 A | 12/2000 |
| JP | 2014-124453 A | 7/2014 |

*Primary Examiner* — Abolfazl Tabatabai
(74) *Attorney, Agent, or Firm* — Global IP Counselors, LLP (57) ABSTRACT

In a biological information acquiring device 10, a sensor module 50 captures a biological image of a subject 2. A touch panel 16 has a display region A11 formed with approximately the same size as a measurement region A13 that matches the range of image capturing of the subject 2 by the sensor module 50, and in the display region A11 a biological image is displayed at approximately the same magnification as the range of image capturing. The image capturing direction of the sensor module 50 and the display direction of the touch panel 16 are in opposite directions, and the measurement region A13 and the display region A11 are arranged in layers at about the same position in a plan view. Accordingly, a target location suitable for acquiring the biological information can be easily specified.

8 Claims, 7 Drawing Sheets

(51) Int. Cl.
 *A61B 5/02* (2006.01)
 *A61B 5/021* (2006.01)
(52) U.S. Cl.
 CPC . *A61B 2560/0475* (2013.01); *A61B 2562/046* (2013.01); *A61B 2576/02* (2013.01)

(56) References Cited

U.S. PATENT DOCUMENTS

2012/0140055 A1* 6/2012 Narusawa .............. G02B 21/10
 348/79
2014/0155767 A1* 6/2014 Fukuda .............. A61B 5/02125
 600/485

* cited by examiner

BIOLOGICAL INFORMATION ACQUIRING DEVICE

BACKGROUND

1. Technical Field

The present invention relates to a biological information acquiring device that acquires biological information of a subject.

2. Related Art

Among devices that acquire biological information of a subject, devices are known that have a sensor or the like put into contact with a skin surface of the subject, and acquire biological information such as blood components by irradiating a measuring light into a living body of the subject. For example, JP-A-2000-189391 and JP-A-2000-339445 each disclose a non-invasive biological inspection device that acquires biological information by analyzing image information obtained by capturing an image of the living body.

In the technology disclosed in JP-A-2000-189391 and JP-A-2000-339445, a detection unit having a built-in image capturing unit grasps a finger, and this detection unit is provided physically separate from a display unit that displays a captured image. Therefore, it is difficult to know the relationship between an image capturing position and a captured image, and thus it is difficult to perform work of changing the image capturing position while viewing captured images to specify a suitable location for acquiring the biological information. This problem is exacerbated by the fact that the range of image capturing is not the same as the size of a displayed image.

SUMMARY

An advantage of some aspects of the invention is that a target location suitable for acquiring biological information can be easily specified.

According to a first aspect of the invention, a biological information acquiring device includes an image capturing unit that captures a biological image of a subject, and a display unit having a display region formed with approximately the same size as a range of image capturing of the subject by the image capturing unit. The display unit displays the biological image in the display region at approximately the same magnification as the range of image capturing. An image capturing direction of the image capturing unit and a display direction of the display unit are in opposite directions, and the range of image capturing and the display region are arranged in layers at about the same position in a plan view.

In the biological information acquiring device according to the first aspect of the invention, the image capturing unit and the display unit are arranged in layers such that the image capturing direction and the display direction are in opposite directions, and the range of image capturing and the display region are at approximately the same position in a plan view. Also, in the display unit, a biological image captured by the image capturing unit is displayed at approximately the same magnification as the range of image capturing of the subject by the image capturing unit. Accordingly, it is possible to display a location of the subject positioned directly under the display region at approximately actual size, and this enables an image capturing target location suitable for acquiring biological information to be easily specified.

In the above biological information acquiring device according to the first aspect of the invention, it is preferable that an amount of offset between an arbitrary image capturing point in the range of image capturing and an arbitrary display point in the display region is not more than 3 mm in a plan view.

In this case, it is possible to set the amount of offset between the range of image capturing and the display region to not more than 3 mm in a plan view.

In the above biological information acquiring device according to the first aspect of the invention, it is preferable that a delay time from capturing of the biological image by the image capturing unit until display of the biological image in the display unit is less than one second.

In this case, it is possible to display a captured biological image in less than one second after capturing that biological image.

In the above biological information acquiring device according to the first aspect of the invention, it is preferable that one frame rate of an image capturing frame rate of the image capturing unit and a display frame rate of the display unit is an integer multiple of the other frame rate.

In this case, it is possible to capture a biological image at the image capturing frame rate and display the captured biological image as video at the display frame rate, and possible to set one frame rate of the image capturing frame rate and the display frame rate when doing so to be an integer multiple of the other frame rate.

In the above biological information acquiring device according to the first aspect of the invention, it is preferable that the image capturing unit is a contact-type image sensor.

In this case, it is possible to use a contact-type image sensor as the image capturing unit.

Alternatively, in the above biological information acquiring device according to the first aspect of the invention, it is preferable that the image capturing unit is an image sensor of a reducing optical system having a reducing optical lens.

In this case, it is possible to use an image sensor of a reducing optical system having a reducing optical lens as the image capturing unit.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
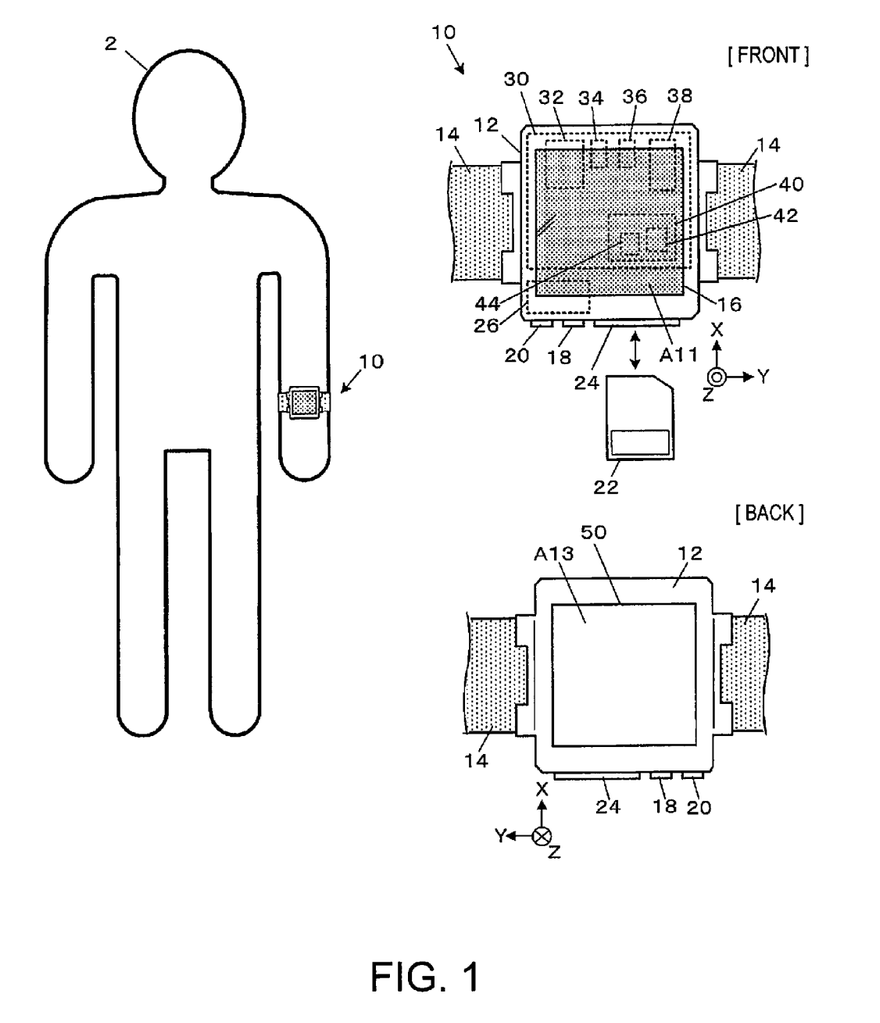
FIG. 1 shows external views showing an exemplary overall configuration of a biological information acquiring device.

The following describes an exemplary embodiment of a biological information acquiring device according to the invention, with reference to the accompanying drawings. The invention is not limited by embodiments described below, and moreover, applicable embodiments of the invention are not limited to those described below. In the accompanying drawings, like numbers reference like elements.

Overall Configuration FIG. 1 shows an exemplary overall configuration of a biological information acquiring device 10 according to the present embodiment. This biological information acquiring device 10 functions as a measuring instrument that non-invasively acquires (measures) biological information of a subject 2, and also functions as a data logger that stores measurement data, and can be considered one type of computer. As shown in FIG. 1, the biological information acquiring device 10 is configured, for example, as a wristwatch-type wearable device, and is used worn on a part of the body of the subject 2 such as an arm, leg, or neck, via a band 14 provided to a main case 12.

The biological information acquiring device 10 includes a touch panel 16 as a display unit on a front face of the main case 12 (the face pointing outwards when worn by the subject 2), and a sensor module 50 as an image capturing unit on the back face of the main case 12 (the face touching skin of the subject 2 when the biological information acquiring device 10 is worn by the subject 2). The touch panel 16 and the sensor module 50 are disposed in layers with the touch panel 16 above and the sensor module 50 below (in direction Z).

The touch panel 16 serves also as an operation input means to input various operations such as starting measurement. Displayed in a display region A11 of the touch panel 16 are, for example, later-described biological images or biological information measurement results.

The sensor module 50 is a main sensor that irradiates an irradiating wave as a measuring light into the living body of the subject 2, and receives a reflected light wave.

On a side face of the main case 12 are provided an operation switch 18 such as a power switch, a communications device 20 capable of detachably connecting with a wired cable for communicating with an external device, and a reader/writer 24 that realizes data reading/writing of a memory card 22. Also, a rechargeable internal battery 26 and a control substrate 30 are provided within the main case 12.

In a case of configuring the communications device 20 to wirelessly communicate with an external device, such a configuration can be realized with a wireless communications module and an antenna.

The memory card 22 is a removable nonvolatile memory capable of rewriting data. Examples of rewritable nonvolatile memory that can be used for the memory card 22 include, other than flash memory, ferroelectric memory (FeRAM: Ferroelectric Random Access Memory) and magnetoresistive memory (MRAM: Magnetoresistive Random Access Memory).

The form of charging the internal battery 26 is selectable as appropriate. For example, a configuration may be adopted in which an electric contact point is separately provided on the back face of the main case 12, and when the main case 12 is placed in a cradle that has been connected to a household power source, powering and charging is performed through the cradle via the electric contact point. Alternatively, a configuration employing non-contact wireless charging may be adopted.

The control substrate 30 performs unified control of the biological information acquiring device 10. The control substrate 30 is equipped with a CPU (Central Processing Unit) 32, a main memory 34, a measurement data memory 36, a touch panel controller IC (Integrated Circuit) 38, and a sensor module controller 40. Other than these, the control substrate 30 can be appropriately equipped with electronic components such as a power management IC or an image processing IC.

The main memory 34 stores a program or initial settings data for example, and is a storage medium capable of storing computational values of the CPU 32. The main memory 34 is realized by appropriately employing, for example, a RAM (Random Access Memory), a ROM (Read-Only Memory), or a flash memory. Also, the program or initial settings data may be stored on the memory card 22.

The measurement data memory 36 is a nonvolatile memory capable of rewriting data, and is a storage medium for storing biological information measurement results. Examples of rewritable nonvolatile memory that can be used for the measurement data memory 36 include, other than flash memory, ferroelectric memory (FeRAM) and magnetoresistive memory (MRAM). Also, measurement data may be stored on the memory card 22.

The touch panel controller IC 38 is an IC that realizes a driver function for displaying an image on the touch panel 16, and also realizes a function for realizing touch input. These functions can be realized by appropriately utilizing publicly known technology together with the touch panel 16.

The sensor module controller 40 has an IC, a circuit or the like responsible for a function of irradiating measuring light with the sensor module 50, and a light-receiving function of receiving measuring light that has been transmitted through biological tissue of the subject 2 (transmitted light), or receiving light that was reflected (reflected light). The sensor module controller 40 includes a light emission controller unit 42 having an IC or a circuit that individually controls light emission by a plurality of light emitting elements (elements that emit measuring light due to application of electric power) provided in the sensor module 50, and a light receiving controller unit 44 having an IC or a circuit that controls reception of light by a plurality of light receiving elements (elements that emit an electrical signal corresponding to an amount of light received) provided in the sensor module 50.

The sensor module controller 40 may be configured with a plurality of ICs. For example, a configuration is also possible in which a separate IC is used for each of the IC or circuit corresponding to the light emission controller unit 42 and the IC or circuit corresponding to the light receiving controller unit 44. Alternatively, a configuration is possible in which some of the functions of those ICs are realized by the CPU 32.

Figure 2A:
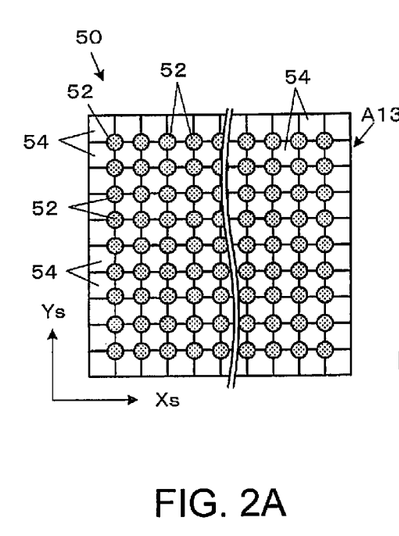
FIGS. 2A and 2B show an exemplary configuration of a sensor module.
Figure 2B:
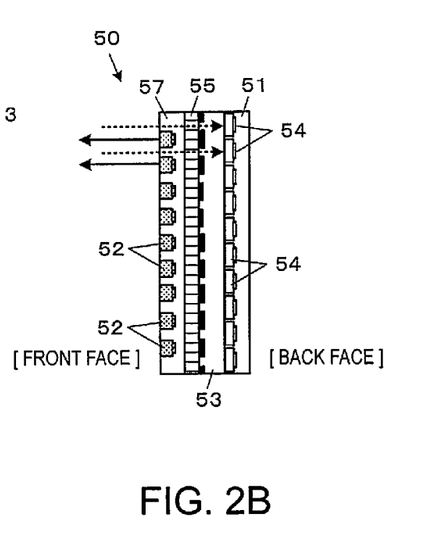

FIGS. 2A and 2B show an exemplary configuration of the sensor module 50. FIG. 2A shows a front view of the sensor module 50 that forms a measurement region A13 where exposure occurs on the back face shown in FIG. 1. FIG. 2B is a cross-sectional view of the sensor module 50. For ease of understanding, light emitting elements 52 and light receiving elements 54 are intentionally shown enlarged. Moreover, the size, aspect ratio, and the like of these elements are not limited by the exemplary configuration shown here, and can be set as appropriate.

The sensor module 50 is a device configured by layering a layer having a plurality of the light emitting elements 52 arranged in a flat plane, and a layer having a plurality of the light receiving elements 54 arranged in a flat plane. Stated another way, the sensor module 50 is an image sensor having a built-in light source, and is a sensor array that realizes functions of both irradiating and receiving measuring light.

The sensor module 50 may also be integrated together with the sensor module controller 40 as a single unit.

Each light emitting element 52 is a light emitting unit that irradiates measuring light, and can be realized by, for example, an LED (Light Emitting Diode) or an OLED (Organic Light Emitting Diode). In a later-described case of measuring a blood glucose level as biological information, it is preferable to use elements capable of emitting light that includes near-infrared light, which is light that is near the visible region and can be transmitted subcutaneously.

Each light receiving element 54 is an imaging element that receives measuring light that has been transmitted subcutaneously or measuring light that was reflected, and outputs an electrical signal corresponding to the amount of light received. The light receiving elements 54 can be realized with, for example, a semiconductor device such as a CCD (Charge Coupled Device) or a CMOS (Complementary Metal Oxide Semiconductor). A single light receiving element 54 is considered to include a plurality of elements that receive the respective wavelength components of RGB.

The sensor module 50 is configured by layering, in order from its base (the back face in FIG. 2B, the front of the main case 12 in FIG. 1):

a light receiving layer 51 where a plurality of the single light receiving elements 54 are arranged in a flat plane and in a grid, a light blocking layer 53 that selectively blocks light other than light directed towards the respective single light receiving elements 54, a spectrum layer 55 that selectively allows transmission of near-infrared light, and a light emitting layer 57 where a plurality of the light emitting elements 52 are arranged in a flat plane and in a grid, between adjacent light receiving elements 54, at positions that do not obstruct an optical path when light that has been transmitted through biological tissue or has been reflected arrives at the light receiving elements 54.

The light receiving elements 54 of the light receiving layer 51 are arranged in the form of a matrix in which pixels can be identified in an Xs-Ys Cartesian coordinate system, and the sensor module 50 functions in a similar manner as a publicly known image sensor. Also, the shape, size, and arrangement pattern of the light receiving elements 54 can be set as appropriate.

The light emitting elements 52 of the light emitting layer 57 are arranged one-by-one in an opposing corner portion of neighboring light receiving elements 54, when viewed from the front face (rear of the main case 12) of the sensor module 50. More specifically, one light emitting element 52 is arranged in an opposing corner portion of four of the light receiving elements 54, and the light emitting elements 52 as a whole are arranged in the form of a matrix in which they can be identified in the same Xs-Ys Cartesian coordinate system as the light receiving elements 54. The sensor module 50 has a driving mechanism that selectively causes the light emitting elements 52 to emit light, and driving of the light emitting elements 52 can be controlled, for example, in a similar manner as an active matrix system of a liquid crystal panel display.

In order to form the sensor module 50 having this sort of layer structure, it is possible to appropriately apply semiconductor micromachining technology used in manufacturing publicly known image sensors or OLED displays.

The size and arrangement interval of the light emitting elements 52 and the size and arrangement interval of the light receiving elements 54 can be set as appropriate. For example, it is suitable to adopt an arrangement interval of 1 to 500 μm, and in order to achieve a balance between production cost and measurement precision, it is possible to adopt an arrangement interval of about 50 to 200 μm, for example. In the sensor module 50, it is also possible to provide a light condensing layer having an additional optical element, with the objective of contracting the range of measuring light emitted from the light emitting elements 52 and polarizing that light, or with the objective of precisely collecting, at the light receiving elements 54, light that has been transmitted through biological tissue or light that was reflected. Also, a protective layer or the like that prevents surface damage may be appropriately provided. Moreover, the invention is not limited to a configuration in which the light emitting elements 52 and the light receiving elements 54 are layered. A configuration may also be adopted in which the light emitting elements 52 and the light receiving elements 54 are arranged side-by-side.

Overview

Figure 3:
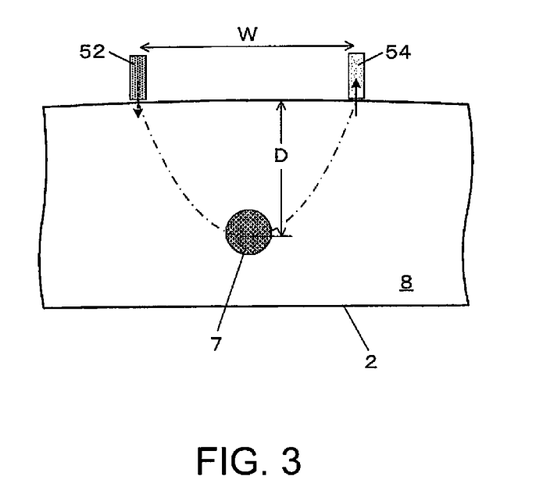
FIG. 3 illustrates propagation of light within a biological tissue.

FIG. 3 illustrates propagation of light within a biological tissue, and shows a cross-sectional view taken in the depth direction of a portion (wearing location) that contacts the measurement region A13 of the subject 2. As shown in FIG. 3, light that has been emitted from a particular light emitting element 52 in the sensor module 50 penetrates into the biological tissue from the skin surface and is diffusely reflected, and a part of that light reaches a particular light receiving element 54. The propagation path of that light forms a kind of banana-like shape (with a region formed between two arcs), with this shape having maximum depth approximately near the center in the depth direction. A depth (reachable depth) D of the propagation path decreases as an interval W between a light emitting element 52 and a light receiving element 54 becomes smaller, and increases as the interval W becomes larger.

Among light (received light) that has been received by the light receiving element 54 in this manner, light that has passed through blood in the course of propagating through biological tissue, i.e. light that has reached a blood vessel 7 and been reflected by blood that flows in the blood vessel 7, or has been absorbed, or has been transmitted through blood, reflects biological information. This biological information is information such as glucose concentration (so-called 'blood glucose level') or oxygen saturation in the blood. Accordingly, by selecting a light emitting element (light emitting element used for measurement) 52 and a light receiving element (light receiving element used for measurement) 54 used for measurement that are suitable for detecting the subcutaneous blood vessel position of the measurement region A13 and receiving light that has passed through the blood, and controlling irradiation and reception of measuring light, it is possible to obtain biological information from the light reception results.

When measuring the biological information, the biological information acquiring device 10 is fixed with the band 14 such that the measurement region A13 of the sensor module 50, which is exposed on the back face of the main case 12, is closely fitted to the skin of the subject 2. By closely fitting the sensor module 50 to the skin, it is possible to suppress main causes of reducing measurement accuracy, namely, reflection of measurement light at the skin surface or scattering of measurement light in tissue near the skin surface.

When the biological information acquiring device 10 is attached to the body of the subject 2 and power is turned on by operating the operation switch 18, image capturing of the subcutaneous biological tissue (subcutaneous tissue) of the measurement region A13 is performed at a predetermined image capturing frame rate (for example, 30 frames per second), and a video biological image is displayed in real time on the touch panel 16 at the same display frame rate as the image capturing frame rate. Here, 'real time' includes a time delay such as needed for signal processing, and indicates a time delay of about one second or less from image capturing of a biological image by the sensor module 50 until that biological image is displayed on the touch panel 16.

In the present embodiment, a biological image is generated in order to detect the position where a blood vessel exists subcutaneously in the measurement region A13 and specify the blood vessel, prior to performing measurement. Also, real time video display of a biological image on the touch panel 16 is performed in order to enable the user of the biological information acquiring device 10 such as the subject 2 or a doctor to know whether a blood vessel exists at the position where the biological information acquiring device 10 is being worn (that is, subcutaneously in the measurement region A13). The procedure for generating this biological image can be performed in the same manner as vein pattern detection in publicly known vein authentication technology, for example. First, the light emitting elements 52 included in the sensor module 50 are all simultaneously caused to emit light, thus irradiating measurement light in the entire area where the biological information acquiring device 10 is being worn as the image capturing range. Then, using all of the light receiving elements 54, light that has been transmitted through the subcutaneous tissue of the measurement region A13 or that has been reflected is received (image capturing is performed), thus generating a biological image. This is repeated at the predetermined image capturing frame rate.

A biological image generated (captured) in this way is a set of luminance data of pixels corresponding to the respective light receiving elements 54 of the sensor module 50, and is obtained as a two-dimensional image in an Xs-Ys Cartesian coordinate system having the same pixel coordinates as the sensor module 50. Due to the effect of blood that flows within a blood vessel, the blood vessel absorbs near-infrared light more easily than portions of biological tissue other than the blood vessel (referred to below as a 'non-blood vessel portion'). Therefore, the blood vessel has less luminance than a non-blood vessel portion and appears darker. Accordingly, by extracting locations of less luminance in the biological image, it is possible to distinguish whether or not a blood vessel or a non-blood vessel portion is shown in each individual pixel. In other words, it is possible to distinguish whether a blood vessel is present under each light receiving element 54.

Figure 4:
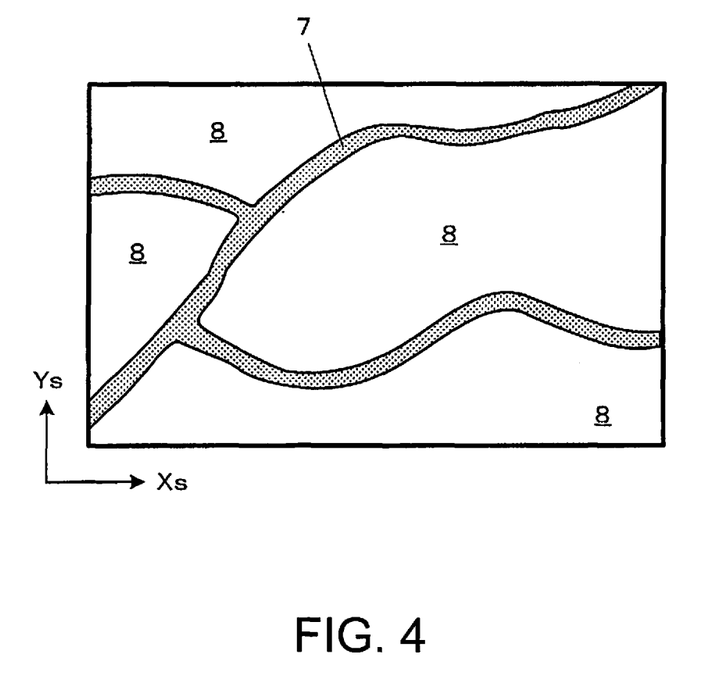
FIG. 4 schematically shows a biological image.

FIG. 4 schematically shows a biological image. In the example shown in FIG. 4, the shaded belt-shaped locations show the blood vessel 7, and the non-darkened locations show non-blood vessel portions 8.

Here, in the present embodiment, the display region A11 of the touch panel 16 has the same size as the measurement region A13 of the sensor module 50. In the touch panel 16 and the sensor module 50, the display direction of the touch panel 16 and the irradiation direction (image capturing direction) of the measuring light irradiated from the sensor module 50 are arranged in opposite directions in the vertical direction, so that the measurement region A13 and the display region A11 are positioned in about the same position in a plan view (viewed from the vertical direction). Also, in the present embodiment, the range of image capturing of the subject 2 by the sensor module 50 matches the measurement region A13.

The number of pixels (number of display dots) in the direction of rows and columns in the touch panel 16 is the same as the number of pixels (number of light receiving elements) in the direction of rows and columns in the sensor module 50, and the touch panel 16 and the sensor module 50 also have the same pixel pitch. Thus there is a one-to-one relationship between the display dots of the display region A11 and the light receiving elements 54 of the sensor module 50. Positioning of the touch panel 16 and the sensor module 50, for example, is performed using alignment marks included in the touch panel 16 and the sensor module 50, such that corresponding display dots and light receiving elements 54 are vertically overlapping.

Accordingly, in the display region A11 of the touch panel 16, the wearing location directly below the display region A11, which is the range of image capturing of the subject 2 by the sensor module 50, has approximately the same magnification. That is, subcutaneous tissue that has been positioned directly below the display region A11 is shown at approximately actual size. One of the frame rates of the image capturing frame rate and the display frame rate in the touch panel 16 is an integer multiple of the other frame rate, and the delay time from image capturing to display is less than one second. Accordingly, a biological image is displayed as a video image in real time in the touch panel 16. Thus, even if a user such as the subject 2 has moved the wearing location of the biological information acquiring device 10 in the midst of an operation, that user can easily know whether or not a blood vessel exists directly beneath the display region A11, in other words at the wearing location prior to movement, based on low-luminance regions of the biological image displayed in an updated manner.

Once the sensor module 50 (and consequently the biological information acquiring device 10) has been positioned appropriately for acquiring biological information in this manner, the biological information acquiring device 10 is fixed to the subject 2 using the band 14.

After positioning of the biological information acquiring device 10, when the position of the blood vessel 7 was detected from the biological image, irradiation and receiving of measuring light are controlled using the selected blood vessel as target, and processing of the light reception results is performed to measure biological information (measurement processing). For example, in a case of measuring blood glucose level as the biological information, the light emitting element 52 used for measurement and the light receiving element 54 used for measurement that were selected according to the position of the blood vessel 7 are selected. Next, measuring light is irradiated from the light emitting element 52 used for measurement, and from the results of light reception (intensity of received light) by the light receiving element 54 used for measurement, a component of light that has been transmitted through the blood vessel is extracted. At this time, for example, a wavelength $\lambda$ of the measuring light is changed within the near-infrared region by changing the wavelength of light emitted by the light emitting element 52, thus generating a light spectrum (absorption spectrum) of vascular transmitted light that has been transmitted through the blood vessel 7 for each wavelength $\lambda$. Thereafter, using a calibration curve that indicates a predetermined relationship between glucose density in the blood and degree of light absorption, the blood glucose level is calculated (estimated) from the absorption spectrum. Note that the technique for calculating the blood glucose level by processing light reception results is not limited to the example technique described above; publicly known technology can also be appropriately adopted. Likewise in the case of measuring other biological information such as oxygen saturation, publicly known technology is preferably adopted as appropriate.

Functional Configuration

Figure 5:
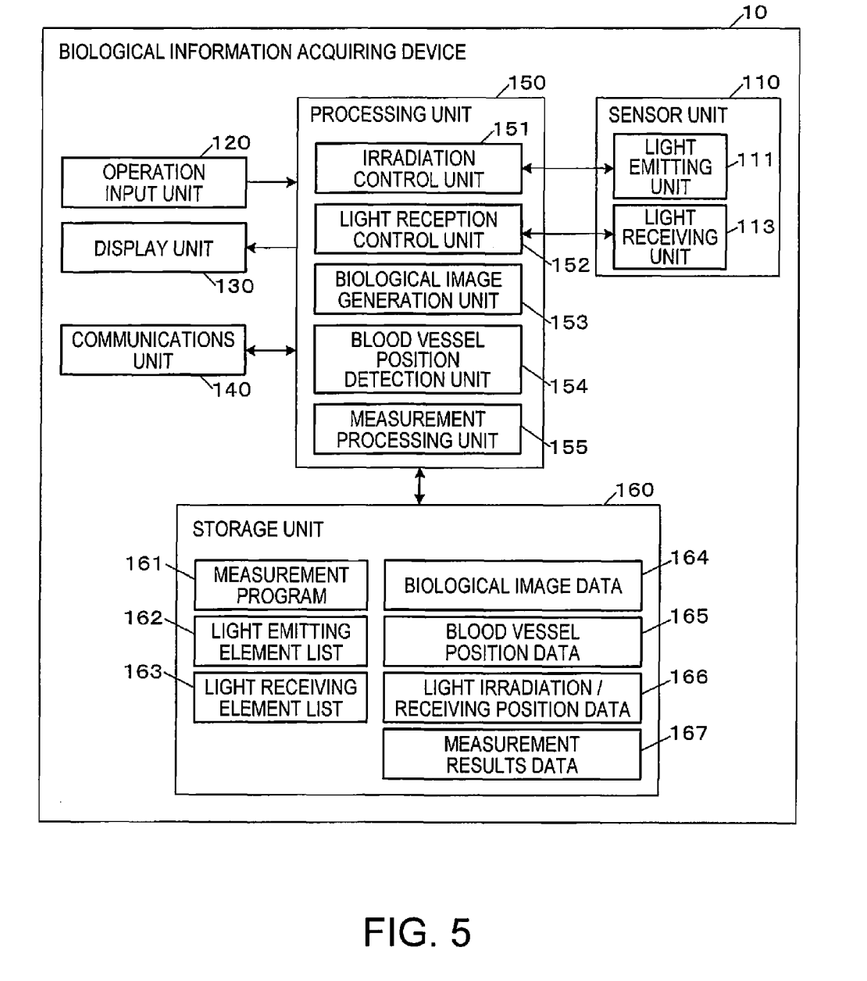
FIG. 5 is a block diagram that shows an exemplary functional configuration of the biological information acquiring device.

FIG. 5 is a block diagram that shows an example of the main functional configuration of the biological information acquiring device 10 according to a first embodiment. As shown in FIG. 5, the biological information acquiring device 10 includes a sensor unit 110, an operation input unit 120, a display unit 130, a communications unit 140, a processing unit 150, and a storage unit 160.

The sensor unit 110 corresponds to the sensor module 50 shown in FIGS. 2A and 2B, and has a light emitting unit 111 configured with a plurality of the light emitting elements 52, and a light receiving unit 113 configured with a plurality of the light receiving elements 54. The arrangement position (Xs-Ys coordinate value) of each light emitting element 52 used to configure the light emitting unit 111 is stored in advance in the storage unit 160 in a light emitting element list 162, in which the arrangement position is associated with a light emitting element number assigned to the corresponding light emitting element 52. Also, the arrangement position (Xs-Ys coordinate value) of each light receiving element 54 used to configure the light receiving unit 113 is stored in advance in the storage unit 160 in a light receiving element list 163, in which the arrangement position is associated with a light receiving element number assigned to the corresponding light receiving element 54.

The operation input unit 120 is realized using an input device such as a touch panel or various switches such as button-type switches or dial-type switches, and outputs an operation input signal to the processing unit 150 according to various operation input performed by the user. The touch panel 16 and the operation switch 18 shown in FIG. 1 correspond to this operation input unit 120.

The display unit 130 is realized using a display device such as an LCD (Liquid Crystal Display) or an EL display (Electroluminescence display), and displays various screens based on a display signal input from the processing unit 150. The touch panel 16 shown in FIG. 1 corresponds to this display unit 130.

The communications unit 140 is a communications device for, under control by the processing unit 150, sending/receiving information internally used by the biological information acquiring device 10 to/from an external information processing device. The communications device 20 shown in FIG. 1 corresponds to this communications unit 140. Various communications systems can be applied as the communications system of the communications unit 140. For example, a wired connection that complies with a prescribed communications standard can be established via a cable, a connection can be established via an intermediate device that also serves as a charger and is referred to as a 'cradle', or a wireless connection can be established using wireless communications.

The processing unit 150 is realized using control and computing devices, for example a microprocessor such as a CPU (Central Processing Unit) or a DSP (Digital Signal Processor), an ASIC (Application Specific Integrated Circuit), or an FPGA (Field-Programmable Gate Array), and performs centralized control of each part of the biological information acquiring device 10. The control substrate 30 shown in FIG. 1 corresponds to this processing unit 150. The processing unit 150 includes an irradiation control unit 151, a light reception control unit 152, a biological image generation unit 153, a blood vessel position detection unit 154, and a measurement processing unit 155. Each unit used to configure the processing unit 150 may also be configured using hardware such as a dedicated module circuit.

The irradiation control unit 151 individually controls emission of light by the light emitting elements 52 included in the light emitting unit 111. For example, the irradiation control unit 151 can be realized using so-called active matrix-type driving control technology. The light reception control unit 152 performs control to read out, from light received by the light receiving elements 54 of the light receiving unit 113, an electrical signal corresponding to the intensity of that received light.

The biological image generation unit 153 performs image capturing of the subcutaneous tissue of the measurement region A13 and generates a biological image (see FIG. 4). The blood vessel position detection unit 154 performs image processing on the biological image to detect the blood vessel position. This biological image capturing and blood vessel position detection can be realized by appropriately using biological image capturing technology or technology for identifying a vein pattern from a biological image, within publicly-known vein authentication technology, for example.

The measurement processing unit 155 causes a light emitting element 52 used for measurement to emit light according to the blood vessel position that was detected by the blood vessel position detection unit 154, and measures biological information using the results of light reception by a light receiving element 54 used for measurement.

The storage unit 160 is realized by a storage medium such as a hard disk or various types of IC memory such as a RAM, a ROM, or a flash memory. The storage unit 160 stores a program for allowing the biological information acquiring device 10 to operate to realize the various functions of the biological information acquiring device 10, and stores data or the like to be used during execution of this program in advance, or temporarily stores such data or the like each time processing is performed. In FIG. 1, the main memory 34 and the measurement data memory 36 built into the control substrate 30, and the memory card 22 correspond to the storage unit 160.

Stored in the storage unit 160 is a measurement program 161 for executing biological information acquisition processing (see FIG. 6) by causing the processing unit 150 to function as the irradiation control unit 151, the light reception control unit 152, the biological image generation unit 153, the blood vessel position detection unit 154, and the measurement processing unit 155. Also stored in the storage unit 160 are the light emitting element list 162, the light receiving element list 163, biological image data 164, blood vessel position data 165, light irradiation/receiving position data 166, and measurement results data 167.

The biological image data 164 stores image data of a biological image that is captured at the predetermined image capturing frame rate. The blood vessel position data 165 stores the position of a blood vessel within the biological image. The light irradiation/receiving position data 166 stores a light emitting element number of a light emitting element 52 used for measurement and a light receiving element number of a light receiving element 54 used for measurement. The measurement results data 167 stores biological information measurement results that have been obtained through measurement processing.

Flow of Processing

Figure 6:
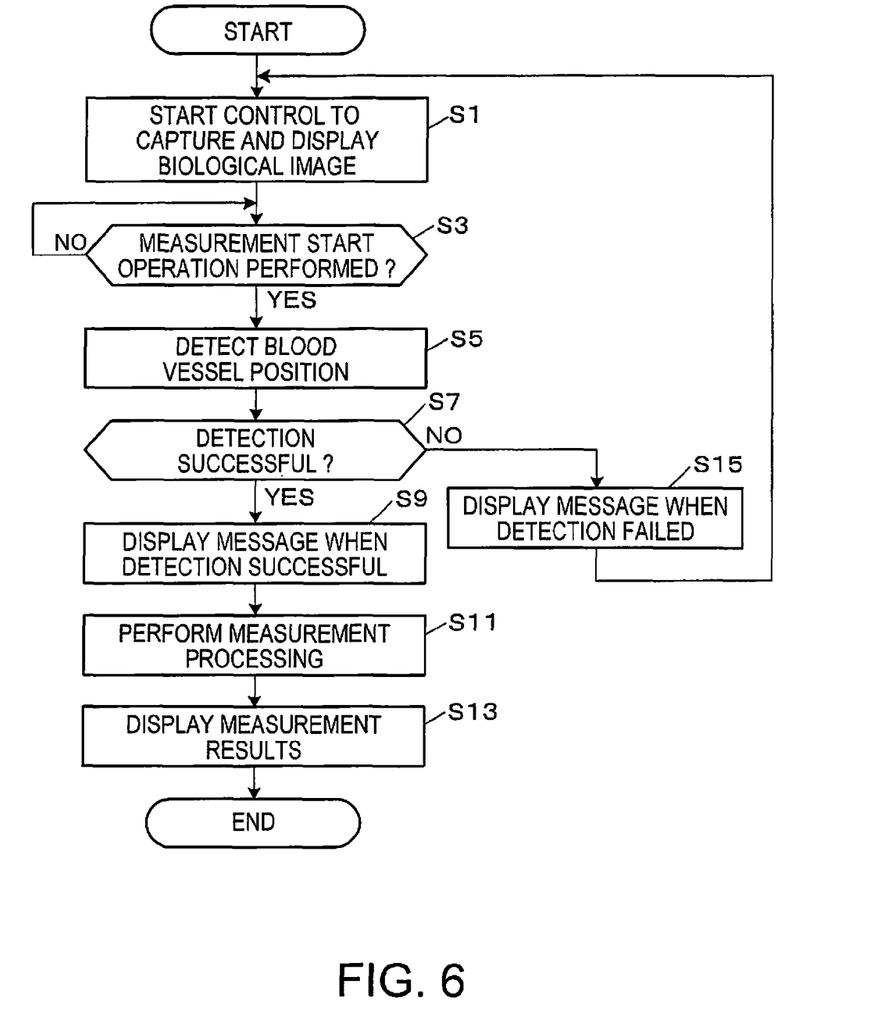
FIG. 6 is a flowchart that shows a processing procedure of biological information acquisition processing.

FIG. 6 is a flowchart that shows the flow of biological information acquisition processing. The processing described here can be realized by the processing unit 150 reading out and executing the measurement program 161 from the storage unit 160. This processing is started when the biological information acquiring device 10 is attached to the body of the subject 2, and the power source of the biological information acquiring device 10 is turned on.

As shown in FIG. 6, in the biological information acquisition processing, first, control is started for the biological image generation unit 153 to continuously perform image capturing of biological images at the predetermined image capturing frame rate, and perform updated display of the generated biological images in the display unit 130 at, for example, the same display frame rate as the image capturing frame rate (Step S1). By the control started here, biological images in which the subcutaneous tissue of the measurement region A13 was captured are displayed as video in real time in the display unit 130. A user such as the subject 2 searches for a blood vessel by appropriately moving the wearing location of the biological information acquiring device 10 while viewing the biological images. After selecting a wearing location where a blood vessel exists and fixing the biological information acquiring device 10 with the band 14, the user inputs a predetermined measurement start operation.

If the measurement start operation has been input (YES in Step S3), after the control started in Step S1 is stopped, the blood vessel position detection unit 154 reads out image data of the newest biological image from the biological image data 164, and performs image processing on the read image data to detect the position of the blood vessel viewed from the skin surface (Step S5). For example, the blood vessel position detection unit 154 detects the blood vessel position by comparing each pixel of the biological image (luminance image) to a reference luminance, and performing processing to convert to a binary value or filter processing. A pixel having less than the reference luminance is deemed to represent the blood vessel, and a pixel having at least the reference luminance is deemed to represent a non-blood vessel portion.

Figure 7:
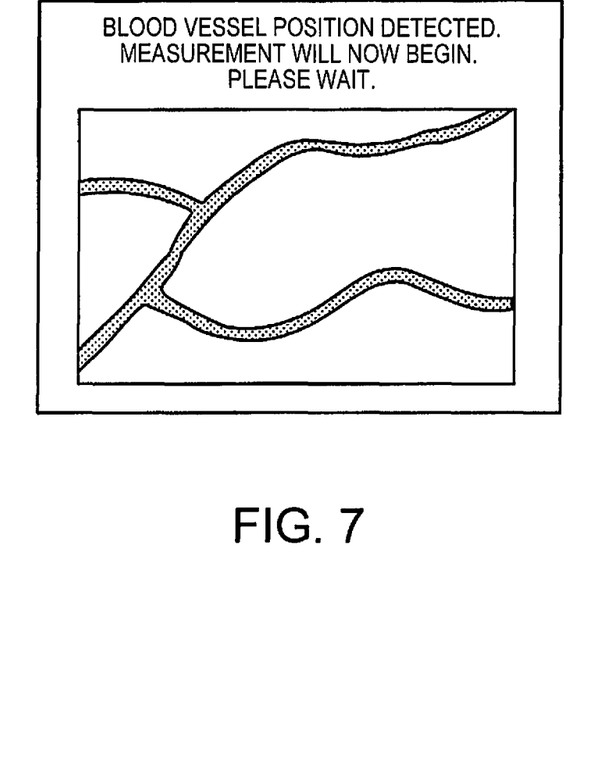
FIG. 7 shows an exemplary display screen.

If detection of the blood vessel position in Step S5 was successful (YES in Step S7), the processing unit 150 performs control to display in the display unit 130 a message that measurement of biological information will begin and also warning the user to be careful not to move the wearing location until measurement ends (Step S9). FIG. 7 shows an exemplary display screen displayed in the display unit 130 in this step. After the measurement start message has been displayed in the display unit 130, the subject 2 waits without moving until measurement ends, as instructed. Afterward, as shown in FIG. 6, the measurement processing unit 155 performs measurement processing to measure the biological information (Step S11). Then, the processing unit 150 performs control to display the biological information measurement results in the display unit 130 (Step S13), and ends main processing.

Regarding the procedure of measurement processing in Step S11, first the measurement processing unit 155 selects the light emitting element 52 used for measurement and the light receiving element 54 used for measurement based on the blood vessel position that has been detected in Step S5. Then, the measurement processing unit 155, based on control by the irradiation control unit 151 and the light reception control unit 152, causes the light emitting element 52 used for measurement to emit (irradiate) measuring light, and generates an absorption spectrum of vascular transmitted light from the results of light reception by the light receiving element 54 used for measurement. Then, the measurement processing unit 155 obtains a blood glucose level from the generated absorption spectrum. The blood glucose level is calculated from the absorption spectrum using, for example, an analysis technique such as multiple regression analysis, principal component regression analysis, PLS (Partial Least Squares) regression analysis, or independent component analysis.

On the other hand, when detection of a blood vessel position failed, such as when a region does not exist where pixels having less than the reference luminance are collected in the biological image (NO in Step S7), the processing unit 150 performs control to display in the display unit 130 a message instructing the user to move the wearing location (Step S15). In addition, the processing unit 150 returns to Step S1, restarts control to capture and display a biological image, and repeats the above-described processing.

Figure 8:
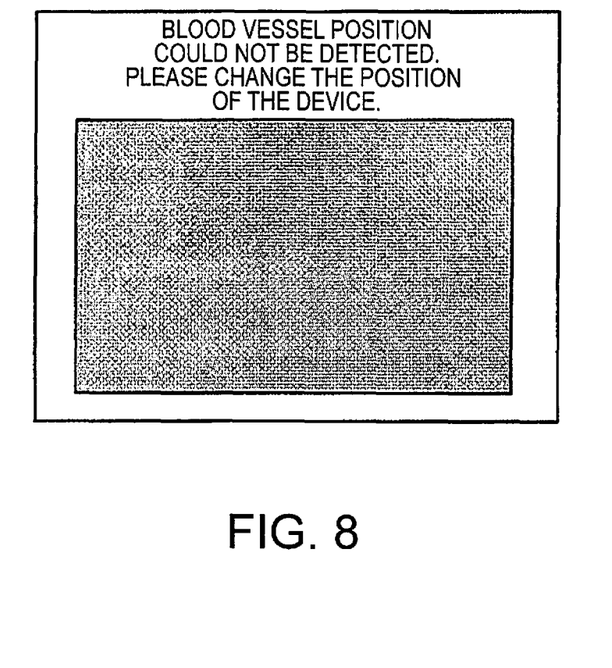
FIG. 8 shows another exemplary display screen.

FIG. 8 shows an exemplary display screen displayed in the display unit 130 by the processing in Step S15. When the message instructing movement of the wearing location has been displayed in the display unit 130, the user such as the subject 2 moves the wearing location of the biological information acquiring device 10 while viewing biological images afterward displayed again as video in the display unit 130, and after again finding a blood vessel, the user inputs the measurement start operation.

As described above, according to the present embodiment, prior to measurement of biological information, a biological image obtained by capturing an image of subcutaneous tissue positioned directly below a display region can be displayed as video at approximately the same magnification (approximately actual size) as that subcutaneous tissue. Accordingly, a user such as the subject 2 can find a blood vessel while viewing the biological image, and then perform the measurement start operation. Therefore, it is possible to suppress a situation in which measurement of biological information is started with the biological information acquiring device 10 being worn at a location where a blood vessel does not exist, thus enabling measurement of biological information to be performed with the blood vessel easily specified.

In the example of the above embodiment, the touch panel 16 and the sensor module 50 have the same number of pixels and the same pixel pitch, but it is not necessary for the number of pixels and the pixel pitch to be the same, if a configuration is adopted in which the range of image capturing of the subject 2 is about the same size as the display region, and the range of image capturing is displayed at approximately equal magnification in the display region.

Also, when desiring to specify a blood vessel as described in the above embodiment, it is preferable that an amount of offset in a plan view is not more than 3 mm between an arbitrary image capturing point (for example, a center point in the image capturing range) in the image capturing range and an arbitrary display point (for example, a center point in the display range) in the display region. Because the maximum width of the blood vessel desired to specify is about 3 mm, it is possible to suppress the risk of overlooking the blood vessel by setting the amount of offset to not more than this width.

Also, in addition to the sensor module 50 described in the above embodiment, a sensor module may also be configured using a contact image sensor (CIS) having an optical lens with 1:1 magnification.

Figure 9:
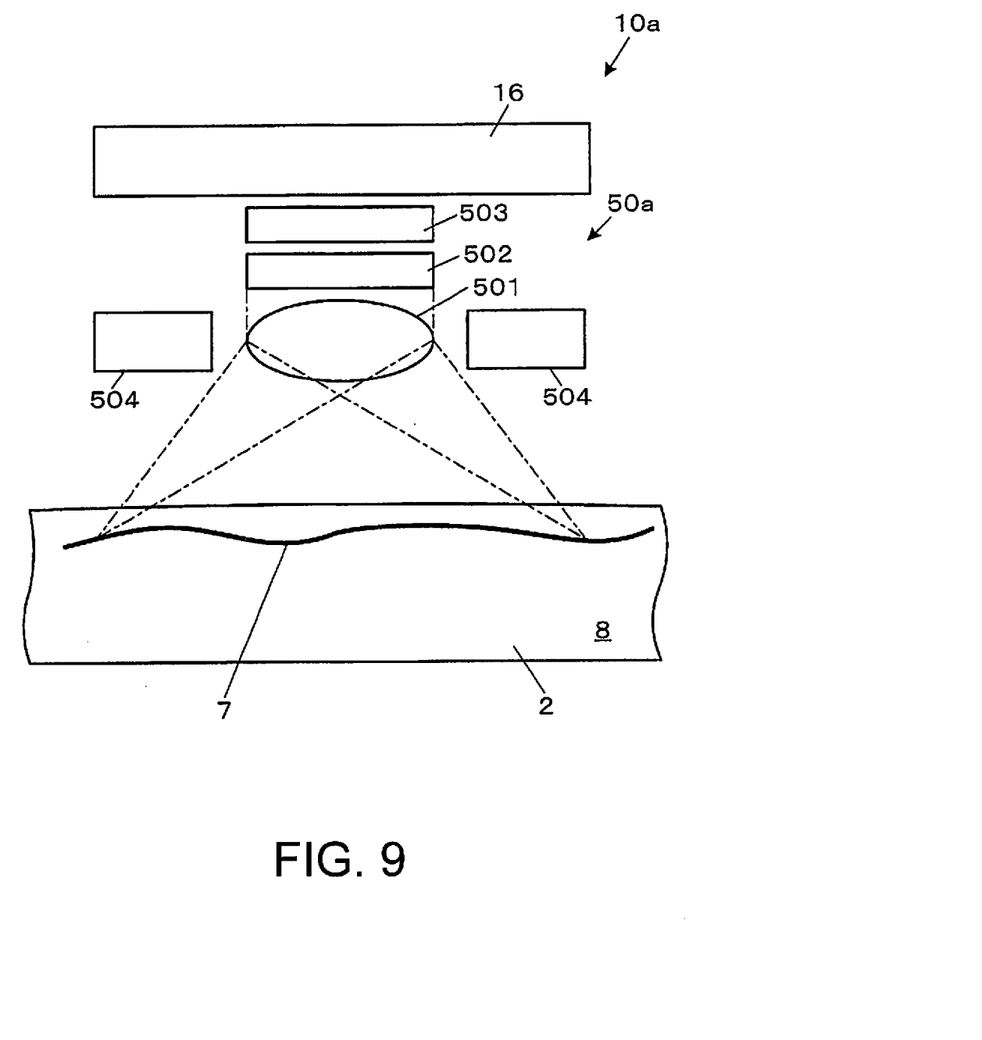
FIG. 9 shows a schematic configuration of a biological information acquiring device according to a modified example.

Alternatively, a sensor module may also be configured using a CCD image sensor having a reducing optical lens. FIG. 9 shows a schematic layer structure of the biological information acquiring device 10 according to this modified example. A biological information acquiring device 10a, similar to the embodiment described above, is configured with the touch panel 16 and a sensor module 50a disposed in layers with the touch panel 16 above and the sensor module 50a below. In this modified example, the sensor module 50a includes a reducing optical lens 501, a variable spectrum substrate 502, an image sensor substrate 503, and LED substrates 504. The variable spectrum substrate 502 has a function corresponding to the spectrum layer 55 shown in FIG. 2B, the image sensor substrate 503 has a function corresponding to the light receiving layer 51 shown in FIG. 2B, and the LED substrates 504 have a function corresponding to the light emitting layer 57 shown in FIG. 2B. Also, the touch panel 16 and the sensor module 50a are designed so that the display region of the touch panel 16 is about the same size as the range of image capturing (range of irradiation of measuring light) of the subject 2 by the sensor module 50a. Therefore, similar to the embodiment described above, a biological image obtained by capturing an image of subcutaneous tissue positioned directly below the display region is displayed in the display region at approximately the same magnification (approximately actual size) as that subcutaneous tissue.

Also, in the embodiment described above, the display frame rate is the same as the image capturing frame rate. However, a configuration may also be adopted in which one of the display frame rate and the image capturing frame rate is an integer multiple of the other frame rate. For example, a configuration may also be adopted in which the image capturing frame rate is set to 10 frames per second, and the display frame rate is set to 30 frames per second, which is three times the image capturing frame rate.

Also, in the embodiment described above, mainly the blood glucose level is measured as the biological information, but the invention is likewise applicable to the measurement of other blood components. For example, the invention is applicable to measurement of the level of enzymes such as GPT (Glutamic Pyruvic Transaminase), the level of plasma proteins such as albumin, the level of cholesterol, or the level of lactic acid.

The invention is also applicable in a case of measuring the condition of internal biological tissue as biological information of the subject 2. For example, the invention is applicable in a case of irradiating an ultrasonic sound wave as the irradiated wave into the living body of the subject, and measuring the diameter of a blood vessel as the condition of internal biological tissue, and also applicable in a case of measuring (estimating) blood pressure from changes in the diameter of a blood vessel.

The entire disclosure of Japanese Patent Application No. 2014-206461 is hereby incorporated herein by reference.

What is claimed is:

1. A biological information acquiring device, comprising:
a sensor that captures a biological image of a subject, the sensor has an image capturing range in which the sensor captures the biological image; and
a display having a display region that has approximately the same size as the image capturing range, the display displaying the biological image in the display region at approximately the same size as the size of the subject for which the biological image is captured,
the sensor and the display being arranged such that an image capturing direction of the sensor is opposite to a display direction of the display, and the image capturing range and the display region are stacked to each other in layers at about the same position in a plan view.

2. The biological information acquiring device according to claim 1,
wherein an amount of offset between an arbitrary image capturing point in the range of image capturing and an arbitrary display point in the display region is not more than 3 mm in a plan view.

3. The biological information acquiring device according to claim 1,
wherein a delay time from capturing of the biological image by the sensor until display of the biological image in the display is less than one second.

4. The biological information acquiring device according to claim 1,
wherein one frame rate of an image capturing frame rate of the sensor and a display frame rate of the display is an integer multiple of the other frame rate.

5. The biological information acquiring device according to claim 1,
wherein the sensor is a contact-type image sensor.

6. The biological information acquiring device according to claim 1,
wherein the sensor is an image sensor of a reducing optical system having a reducing optical lens.

7. A biological information acquiring device, comprising:
a display where a biological image is displayed; and
a processing circuit that detects a blood vessel position from the biological image and controls the display
in response to successful detection of the blood vessel position, the processing circuit displaying in the display a message warning not to move the position of the biological information acquiring device until measurement of biological information ends, and after the measurement has ended, the processing circuit further displaying in the display results of the measurement, and
in response to failed detection of the blood vessel position, the processing circuit displaying in the display a message instructing to move the position of the biological information acquiring device.

8. The biological information acquiring device according to claim 7,
wherein the processing circuit detects the blood vessel position by, for each pixel of the biological image, determining that a pixel having less than a predetermined luminance is a blood vessel portion, and determining that a pixel having at least the predetermined luminance is a non-blood vessel portion.

* * * * *